United States Patent
Gaines et al.

(10) Patent No.: US 7,092,797 B2
(45) Date of Patent: Aug. 15, 2006

(54) FLOW MONITORING SYSTEM FOR A FLOW CONTROL APPARATUS

(75) Inventors: Robert B. Gaines, Lake St. Louis, MO (US); Joseph A. Hudson, O'Fallon, MO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 10/853,926

(22) Filed: May 25, 2004

(65) Prior Publication Data
US 2005/0278072 A1  Dec. 15, 2005

(51) Int. Cl.
*G05D 7/00* (2006.01)
(52) U.S. Cl. ............... 700/282; 604/65; 604/67
(58) Field of Classification Search ............... 700/282; 604/65, 153, 152, 67; 73/703
See application file for complete search history.

(56) References Cited

U.S. PATENT DOCUMENTS

| | | | |
|---|---|---|---|
| 4,504,263 A | 3/1985 | Steuer et al. | |
| 4,583,975 A | 4/1986 | Pekkarinen et al. | |
| 4,820,281 A | 4/1989 | Lawler, Jr. | |
| 4,845,487 A * | 7/1989 | Frantz et al. | 340/679 |
| 4,869,722 A | 9/1989 | Heyman | |
| 4,959,050 A | 9/1990 | Bobo, Jr. | |
| 5,039,279 A | 8/1991 | Natwick et al. | |
| 5,049,047 A | 9/1991 | Polaschegg et al. | |
| 5,135,485 A | 8/1992 | Cohen et al. | |
| 5,213,573 A | 5/1993 | Sorich et al. | |
| 5,292,306 A * | 3/1994 | Wynkoop et al. | 604/505 |
| 5,423,746 A | 6/1995 | Burkett et al. | |
| 5,438,510 A | 8/1995 | Bryant et al. | |
| 5,464,392 A | 11/1995 | Epstein et al. | |
| 5,551,850 A | 9/1996 | Williamson et al. | |
| 5,562,615 A | 10/1996 | Nassif | |
| 5,563,584 A | 10/1996 | Rader et al. | |
| 5,584,811 A | 12/1996 | Ross et al. | |
| 5,695,473 A * | 12/1997 | Olsen | 604/153 |
| 5,720,721 A | 2/1998 | Dumas et al. | |
| 5,807,322 A * | 9/1998 | Lindsey et al. | 604/65 |
| 5,843,035 A | 12/1998 | Bowman et al. | |
| 5,853,386 A * | 12/1998 | Davis et al. | 604/65 |
| 5,943,633 A | 8/1999 | Wilson et al. | |
| 5,951,510 A | 9/1999 | Barak | |
| 6,068,612 A | 5/2000 | Bowman et al. | |
| RE36,871 E | 9/2000 | Epstein et al. | |
| 6,203,528 B1 * | 3/2001 | Deckert et al. | 604/131 |
| 6,280,408 B1 | 8/2001 | Sipin | |
| 6,491,661 B1 | 12/2002 | Boukhny et al. | |
| 6,523,414 B1 * | 2/2003 | Malmstrom et al. | 73/705 |
| 6,622,542 B1 * | 9/2003 | Derek et al. | 73/19.03 |
| 6,890,291 B1 | 5/2005 | Robinson et al. | |
| 6,942,637 B1 | 9/2005 | Cartledge et al. | |
| 2002/0151838 A1 | 10/2002 | Beck et al. | |

FOREIGN PATENT DOCUMENTS

| | | | |
|---|---|---|---|
| EP | 1 466 637 A2 | 10/2004 | |
| EP | 1466637 A2 * | 10/2004 | |

(Continued)

*Primary Examiner*—Albert W. Paladini
*Assistant Examiner*—Steven R. Garland

(57) ABSTRACT

A flow control apparatus having a flow monitoring system capable of detecting and identifying flow present within the administration feeding set loaded to the flow control apparatus is disclosed. The flow control apparatus comprises a single sensor capable of detecting the presence or absence of fluid in the administration feeding set. A software subsystem may be operatively associated with the single sensor that is capable of identifying between upstream and downstream flow conditions present within the administration feeding set loaded to the flow control apparatus.

10 Claims, 7 Drawing Sheets

FOREIGN PATENT DOCUMENTS

| | | |
|---|---|---|
| WO | PCT/US95/09440 | 2/1996 |
| WO | PCT/US01/45621 | 10/2001 |
| WO | PCT/US01/09893 | 3/2002 |

* cited by examiner

FLOW MONITORING SYSTEM FOR A FLOW CONTROL APPARATUS

FIELD OF THE INVENTION

The present invention relates to a flow control apparatus capable of identifying flow conditions present within an administration feeding set.

BACKGROUND OF THE INVENTION

Administering fluids containing medicine or nutrition to a patient is generally well known in the art. Typically, fluid is delivered to the patient by an administration feeding set loaded to a flow control apparatus, such as a pump, connected to a source of fluid which delivers fluid to a patient.

A flow control apparatus of the prior art may also be capable of monitoring and detecting fluid flow conditions that can occur within the loaded administration feeding set during operation of the flow control apparatus. Generally, prior art flow monitoring systems that are capable of monitoring and detecting flow conditions may rely on separate sensors being placed at the upstream and downstream sides of the administration feeding set in order to distinguish between an upstream or a downstream flow condition.

Therefore, there is a need in the art for an improved flow control apparatus having a flow monitoring system capable of identifying between an upstream flow condition and a downstream flow condition using a single sensor, thereby making it possible to monitor the flow of the fluid and recognize any problem that has occurred in the delivery of the fluid.

SUMMARY OF THE INVENTION

The present invention relates to a flow control apparatus comprising a flow control apparatus adapted to be loaded with an administration feeding set having an upstream side and a downstream side, a single sensor for detecting the presence or absence of fluid in the upstream side of the administration feeding set, and a software subsystem in operative association with the single sensor, wherein the software subsystem is capable of identifying between an upstream flow condition and a downstream flow condition present within the administration feeding set.

The present invention also relates to a flow control apparatus comprising a flow control apparatus adapted to be loaded with an administration feeding set, an administration feeding set having an upstream side and a downstream side with the administration feeding set loaded to the flow control apparatus, a single sensor for detecting the presence or absence of fluid in the upstream side of the administration feeding set, and a software subsystem in operative association with the single sensor, wherein the software subsystem is capable of identifying between an upstream flow condition and downstream flow condition present within the administration feeding set loaded to the flow control apparatus.

The present invention further relates to a method for monitoring fluid flow comprising engaging one end of an administration feeding set to at least one fluid source, loading the administration feeding set to a flow control apparatus, engaging another end of the administration feeding set, and identifying between an upstream flow condition and a downstream flow condition present within the administration feeding set loaded to the flow control apparatus.

DETAILED DESCRIPTION OF THE INVENTION

Figure 1:
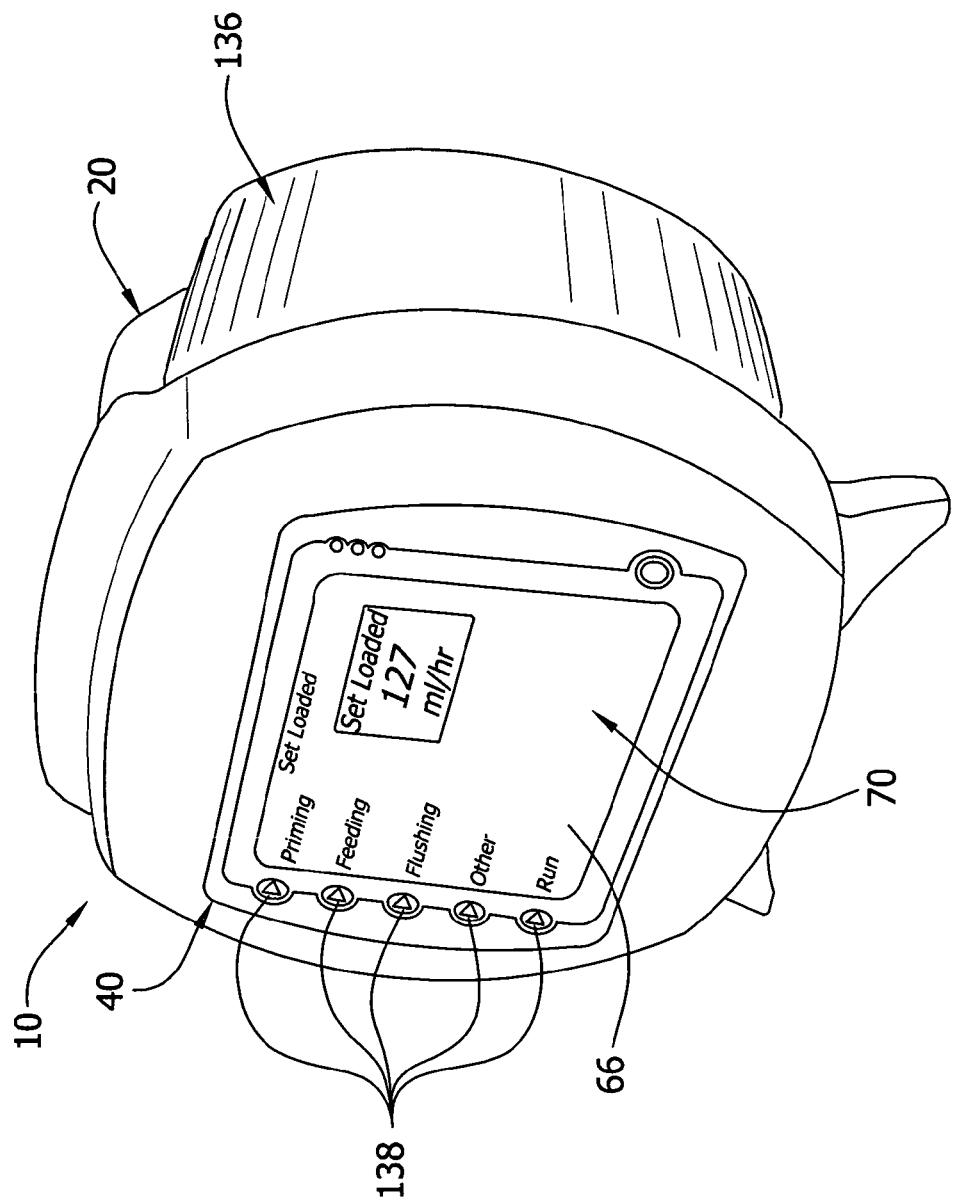
FIG. 1 is a perspective view of an exemplary flow control apparatus having a flow monitoring system according to the present invention.

Referring to the drawings, an embodiment of the flow control apparatus according to the present invention is illustrated and generally indicated as 10 in FIGS. 1–5. Flow control apparatus 10 comprises a flow monitoring system 12 that is capable of detecting and identifying between upstream and downstream flow conditions present within an administration feeding set 14. The administration feeding set 14 includes tubing 56 that is loaded to the flow control apparatus 10 for delivery of fluid to a patient by engaging a valve mechanism 26 and mounting member 74 of the administration feeding set 14 to the flow control apparatus 10. As used herein, the term load means that the valve mechanism 28 and mounting member 74 are engaged to the flow control apparatus 10 and tubing 56 is placed in a stretched condition between the valve mechanism 28 and mounting member 74 such that the administration feeding set 14 is ready for operation with flow control apparatus 10.

Figure 2:
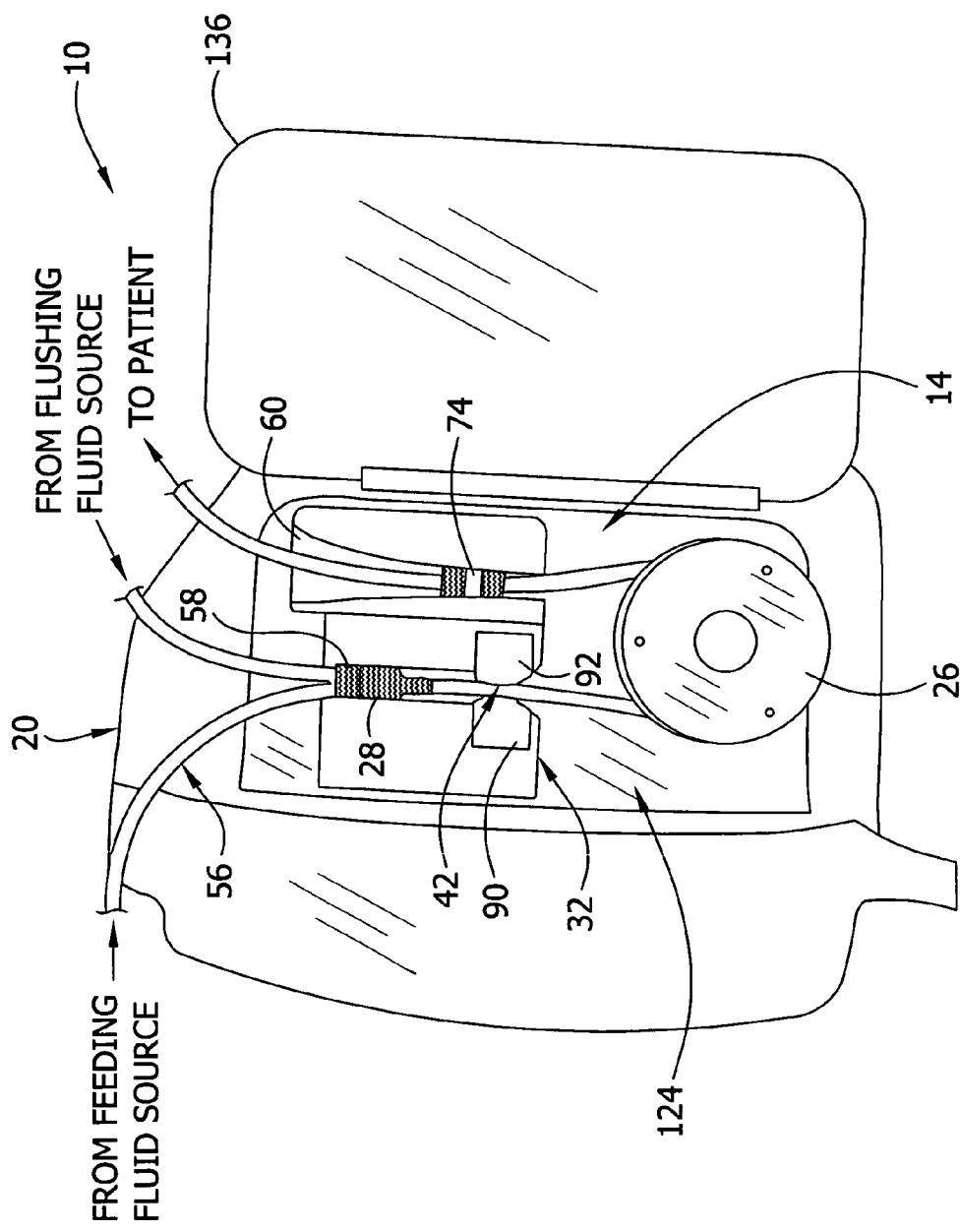
FIG. 2 is a side view of the flow control apparatus with an administration feeding set loaded thereto according to the present invention.

Referring to FIGS. 1 and 2, an exemplary flow control apparatus 10 according to the present invention comprises a housing 20 adapted for loading administration feeding set 14 to the flow control apparatus 10. Flow control apparatus 10 comprises a main recess 124 covered by a main door 136 and includes first and second recesses 58 and 60 for providing sites that are adapted to load the administration feeding set 14 to the flow control apparatus 10 when engaging the valve mechanism 28 and mounting member 74 to first and second recesses 58, 60, respectively. Preferably, a means for driving fluid, such as a rotor 26, is rotatably engaged through housing 20 and adapted to engage tubing 56 such that tubing 56 is placed in a stretched condition between first and second recesses 58, 60 when the administration feeding set 14 is loaded to the flow control apparatus 10.

As used herein, the portion of tubing 56 of administration feeding set 14 leading to rotor 26 is termed upstream, while the portion of tubing 56 leading away from rotor 26 is termed downstream. Accordingly, rotation of rotor 26 compresses tubing 56 and provides a means for driving fluid from the upstream to the downstream side of the administration feeding set 14 for delivery to a patient. The present invention contemplates that any flow control apparatus having a means for driving fluid may be used, such as a linear peristaltic pump, bellows pump, turbine pump, rotary peristaltic pump, and displacement pump. In addition, the present invention contemplates that a means for preventing fluid flow in the administration feeding set 14 is preferably valve mechanism 28; however any means that can prevent fluid flow through the administration feeding set 14 may be used.

Referring to FIG. 1, flow control apparatus 10 further comprises a user interface 40 that assists the user to operatively interface with the flow control apparatus 10. A display 70, in operative association with a plurality of buttons 138 positioned along an overlay 66, assist the user to interact with a microprocessor 62 to operate the flow monitoring system 12 according to the present invention.

Figure 3:
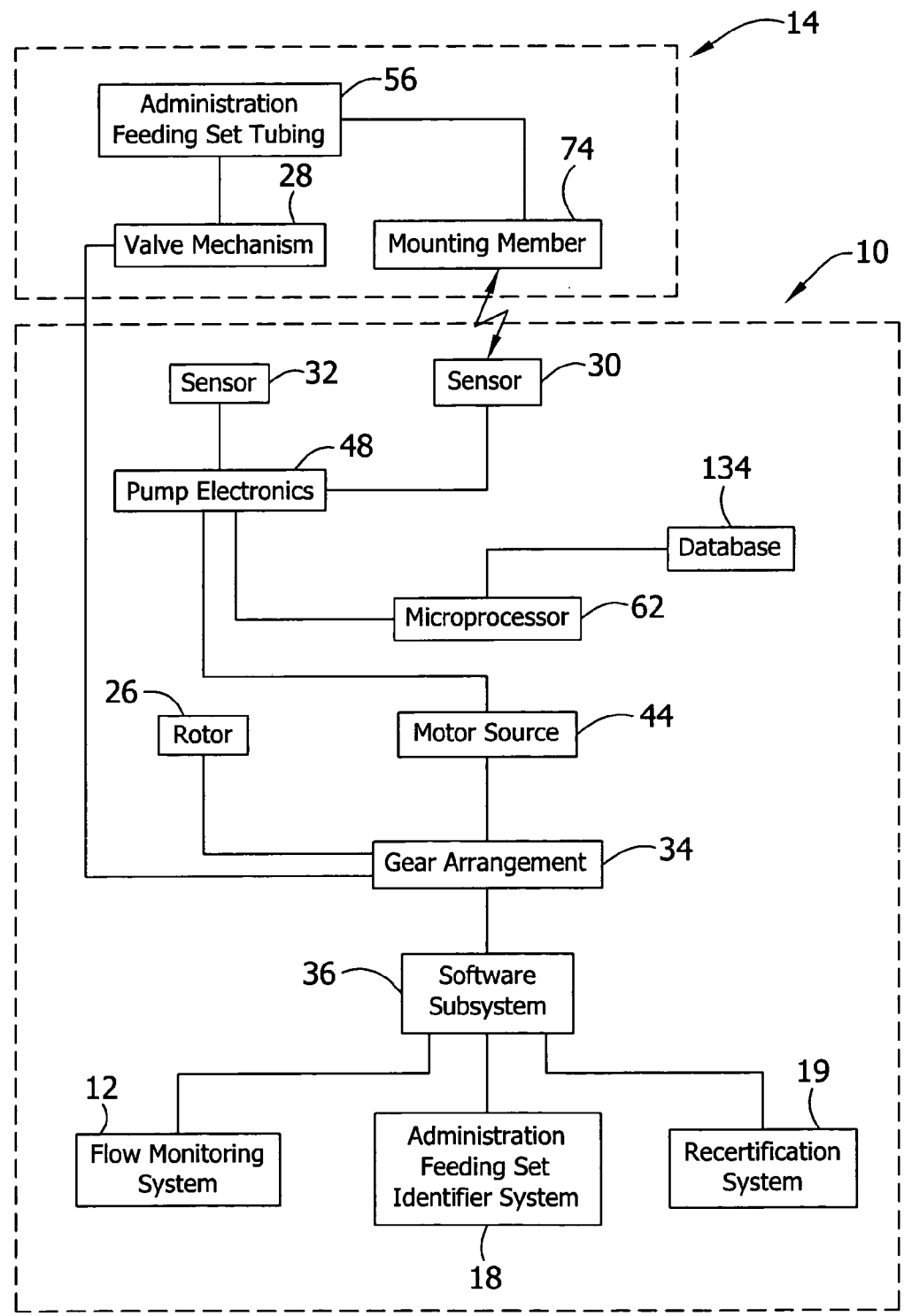
FIG. 3 is a simplified block diagram illustrating the elements of the flow control apparatus comprising a flow monitoring system according to the present invention.

Referring to FIG. 3, flow control apparatus 10 further comprises a microprocessor 62 in operative association with a single sensor 32. A software subsystem 36 is operatively associated with microprocessor 62 and is further associated with flow monitoring system 12 and a means for preventing fluid flow, such as valve mechanism 28, that provides a means for the flow control apparatus 10 to detect and identify between upstream and downstream flow conditions present in the administration feeding set 14 during operation of the flow control apparatus 10. As noted above, flow control apparatus 10 includes single sensor 32 for detecting whether fluid is present or absent in tubing 56 at the upstream side of the administration feeding set 14. The single sensor 32 is located on housing 20 of the flow control apparatus 10 and is positioned to detect the presence or absence of fluid in the upstream side of the administration feeding set 14. In an embodiment shown in FIG. 2, single sensor 32 is incorporated in a recessed sensor track 42 and is adapted to securely receive tubing 56 therein when the administration feeding set 14 is loaded to the flow control apparatus 10.

In order for single sensor 32 to detect the presence or absence of fluid in the tubing 56 of the administration feeding set 14 it is required that tubing 56 be engaged and retained within sensor track 42. In one embodiment, the engagement and retention of tubing 56 within sensor track 42 is achieved by activating flow control apparatus 10 when tubing 56 is empty of fluid and engaged around the flow control apparatus 10 such that a vacuum is created that decreases the outer diameter of tubing 56 as air is evacuated from the administration feeding set 14, thereby placing tubing 56 in a deflated state. In this deflated state, the user may easily insert tubing 56 within sensor track 42 when loading the administration feeding set 14 to the flow control apparatus 10.

Further, with tubing 56 empty of any fluid, a valve mechanism 28 connected to tubing 56 is engaged to the first recess 58, the tubing 56 then wrapped around rotor 26, and a mounting member 74 engaged to second recess 60 such that administration feeding set 14 is loaded to flow control apparatus 10 and the portion of tubing 56 between first and second recesses 58 and 60 is in a stretched condition. Valve mechanism 28 is then operated to allow fluid flow communication through tubing 56 such that air is evacuated from the administration feeding set 14. Thus, when the rotor 26 is made operational during this priming procedure a vacuum is created within tubing 56 forcing it to collapse due to the flexible nature of tubing 56 and lack of fluid contained in the administration feeding set 14. This temporary collapse of tubing 56 coupled with the tensile forces applied from operating rotor 26 allows tubing 56 to be easily retained within sensor track 42.

In addition, when the flow control apparatus 10 is operational and the tubing 56 engaged within sensor track 42, fluid flow through tubing 56 increases the outer diameter of tubing 56 relative to the inner diameter of the sensor track 42. Once the tubing 56 is engaged within sensor track 42 and the remaining portions of the administration feeding set 14 are engaged to flow control apparatus 10, the flow monitoring system 16 becomes operational.

Microprocessor 62 controls and manages the operation of the various components of the flow control apparatus 10. Preferably, single sensor 32 comprises an ultrasonic transmitter assembly 90 that transmits an ultrasonic signal through the portion of tubing 56 seated in the sensor track 42 to provide a means for detecting the presence or absence of fluid in the upstream side of the administration feeding set 14 when the signal is received by a receiver assembly 92. Upon receipt of the ultrasonic signal, receiver assembly 92 detects whether fluid is present or absent within tubing 56 along sensor track 42 based on the characteristics of the ultrasonic signal received by the microprocessor 62. The receiver assembly 92 then communicates with the microprocessor 62. Based on the characteristics of the received ultrasonic signal communicated to microprocessor 62 software subsystem 36 determines whether fluid flow within the administration feeding set 14 is normal or a flow abnormality exists.

Software subsystem 36 determines through a series of decision points and steps whether normal flow or abnormal flow conditions exist within tubing 56, and if an abnormal flow condition does exist, whether it is a bag empty condition, upstream occlusion, or a downstream occlusion.

Figure 4:
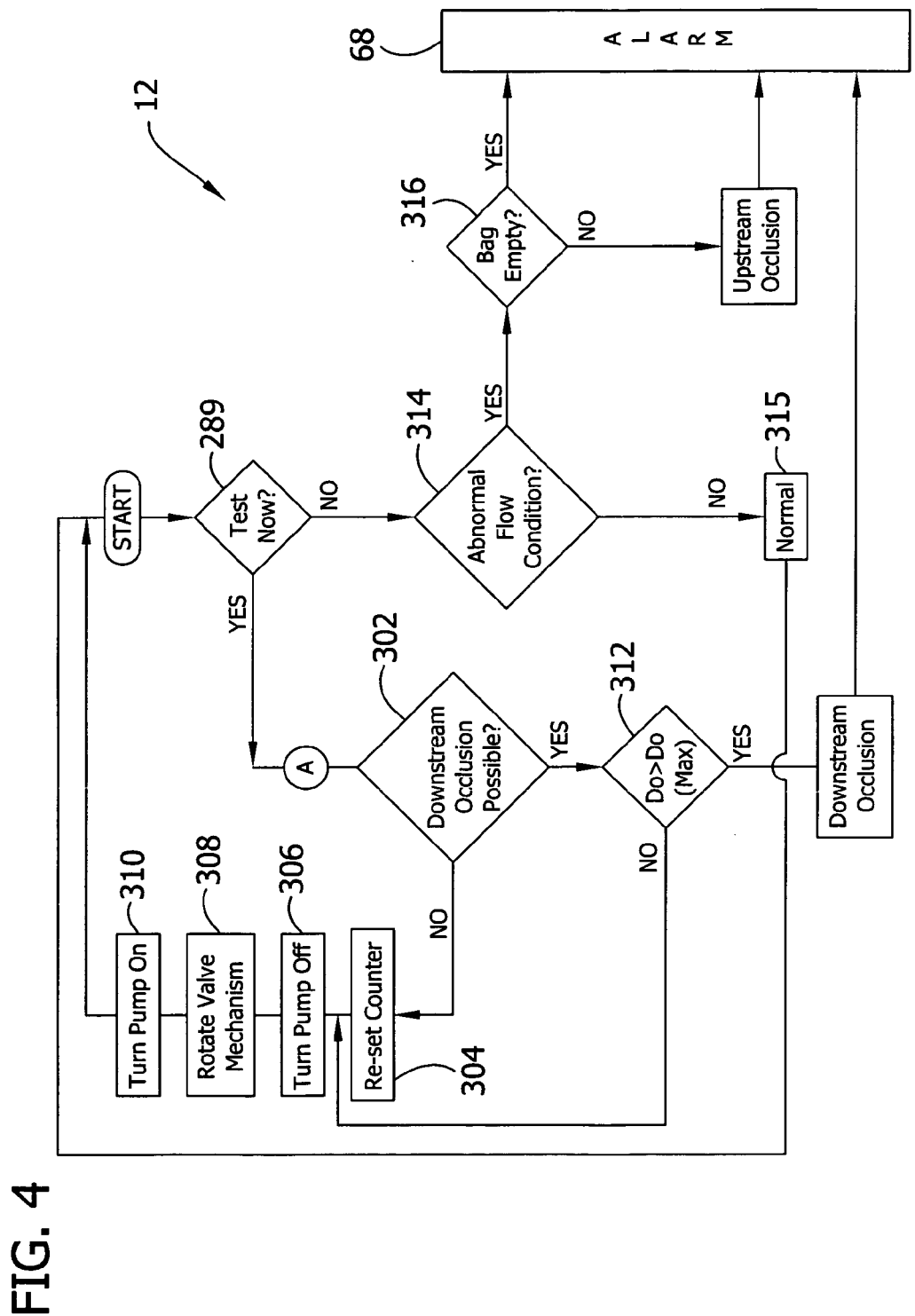
FIG. 4 is a flow chart of the flow monitoring system according to the present invention.
Figure 4A:
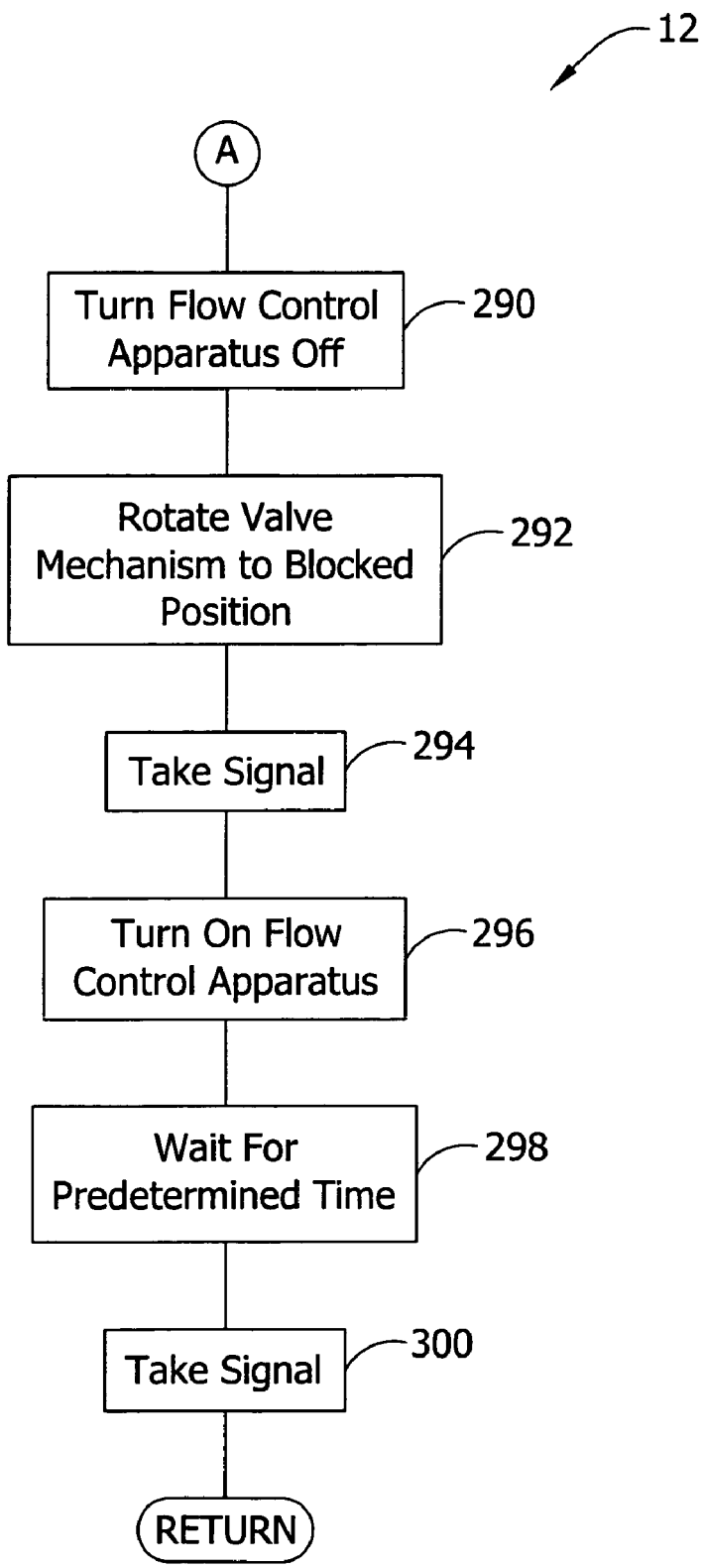
FIG. 4A is a sub-routine of the flow chart shown in FIG. 4 according to the present invention.

Referring to the flow charts in FIGS. 4 and 4A, the various decision points and steps executed by software subsystem 36 to perform an intermittent test procedure A by flow monitoring system 12 are illustrated. Software subsystem 36 directs flow control apparatus 10 to perform various operations related to detecting and distinguishing between upstream and downstream flow conditions present in the administration feeding set 14. During normal operation, single sensor 32 transmits ultrasonic signals through tubing 56 engaged within sensor track 42 for detecting the presence or absence of fluid in the administration feeding set 14. During operation of flow control apparatus 10 software subsystem 36 decides at predetermined times whether to initiate an intermittent test procedure A to determine whether a downstream occlusion exists. Intermittent test procedure A comprises terminating fluid flow communication through the administration feeding set 14 by valve mechanism 28, transmitting and detecting an ultrasonic wave for determining the presence or absence of fluid by single sensor 32 and a repetition of these steps, if necessary.

In particular, at step 289 software subsystem 36 decides whether to perform the intermittent test procedure A as illustrated in FIG. 4A. If so, the microprocessor 62 instructs flow control apparatus 10 to the OFF condition at step 290 in order to terminate operation of flow control apparatus 10 such that rotor 26 no longer drives fluid through tubing 56. At step 292, microprocessor 62 then places valve mechanism 28 in the blocking position that prevents fluid flow through tubing 56.

After fluid flow has been prevented through the administration feeding set 14 by valve mechanism 28, a baseline signal is taken by the single sensor 32 at step 294 for providing microprocessor 62 with a reading of the signal when the flow control apparatus 10 is reactivated at step 296. After re-activation, any fluid present within tubing 56 should be driven through tubing 56 by operation of rotor 26 and delivered to the patient as long as no occlusion is present along the downstream side of the administration feeding set 14. After a short period of time placement of valve mechanism 28 in the blocking position that terminates fluid flow should cause tubing 56 to run dry of any remaining fluid unless a downstream occlusion is present which would effectively prevent fluid from being delivered to the patient as fluid is forced to remain within tubing 56 due to the occlusion. Software subsystem 36, after a predetermined amount of time, permits any excess fluid to drain from tubing 56 at step 298. At step 300, single sensor 32 then transmits another ultrasonic signal through tubing 56 and takes a second reading to determine if fluid is present or absent within the administration feeding set 14. If fluid remains within the administration feeding set 14, software subsystem 36 then determines that a downstream occlusion is present and sounds an alarm.

Once intermittent test procedure A is completed, software subsystem 36 reaches a decision point 302 which determines whether or not a downstream flow condition, such as an occlusion along the downstream side of the administration feeding set 14 is present within tubing 56. If no fluid remains in tubing 56 at decision point 302, software subsystem 36 determines that no downstream occlusion is present. At step 304, microprocessor 62 re-sets the counter and places flow control apparatus 10 in an OFF condition at step 306. Valve mechanism 28 is then placed in either a feeding or flushing position that permits fluid flow through tubing 56 at step 308. After actuation of valve mechanism 28 to the feed or flush position flow control apparatus 10 is placed in the ON condition at step 310 and the flow monitoring system 12 has software subsystem 36 return to step 289.

If at decision point 302 an occlusion along the downstream side of the administration feeding set 14 is possible then decision point 312 is reached. Decision point 312 counts the number of occurrences that single sensor 32 detects the presence of fluid within tubing 56 which is referred to as $D_o$, while a pre-set maximum number of occurrences that flow monitoring system 12 allows for detection of a possible downstream occlusion being referred to as $D_o(max)$. If the $D_o$ is not greater than $D_o(max)$ at decision point 312 software subsystem 36 will determine that no downstream occlusion exists and valve mechanism 28 is placed in a position that permits fluid flow through the administration feeding set 14 in a manner as previously described above in steps 304, 306, 308, and 310. However, if $D_o$ is greater than $D_o(max)$ a downstream occlusion may exist and software subsystem 36 will direct microprocessor 62 to activate an alarm 68.

Preferably, alarm 68 may be audible, visual, vibratory or any combination thereof. In an embodiment of the present invention it is anticipated that a certain type of alarm 68 may represent a specific abnormal flow condition being present within administration feeding set 14 and identifiable to the user by its own unique visual, audible and/or vibratory alarm 68. For example, alarm 68 having different sounds could indicate different types of upstream and downstream flow conditions, such as a downstream occlusion, a bag empty condition, or an upstream occlusion. These unique alarms 68 allow for flow monitoring system 12 to signal the presence of several different abnormal flow conditions.

The detection of the upstream flow conditions present within administration feeding set 14, such as upstream occlusion or a bag empty condition, is determined by the presence or absence of fluid within tubing 56 by single sensor 32 at a detection point positioned on the upstream side of administration feeding set 14. However, unlike the detection of a downstream occlusion along the administration feeding set 14 the detection of an upstream flow condition, such as an upstream occlusion or bag empty condition, in the administration feeding set 14 does not require that the intermittent test procedure A be performed. Instead, the detection of these upstream flow conditions is accomplished during the normal operation of flow control apparatus 10 while valve mechanism 28 is in the feeding or flushing position that permits fluid flow through the administration feeding set 14.

Flow monitoring system 12 also detects and distinguishes between upstream flow conditions, such as normal flow, bag empty, and upstream occlusion conditions when the intermittent testing procedure A is not being performed by software subsystem 36. Specifically, at decision point 289 if software subsystem 36 does not initiate intermittent test procedure A for detecting downstream flow conditions software subsystem 36 will function to detect and distinguish between the conditions of normal flow, bag empty, and upstream occlusion.

Software subsystem 36 in operative association with flow monitoring system 12 determines whether or not a normal upstream flow condition exists within administration feeding set 14 during operation of flow control apparatus 10. This operation occurs at a decision point 314 and is determined based upon the presence or absence of fluid as detected by the single sensor 32. Specifically, if single sensor 32 detects the presence of fluid within tubing 56 then the flow is detected by software subsystem 36 at decision point 314. A normal upstream flow condition exists because a flow condition is not present that would occlude or obstruct fluid flow on the upstream side of the administration feeding set 14 that would cause fluid to become absent as detected by the single sensor 32. If flow is present at decision point 314 this normal flow condition would be displayed on user interface 40 at step 315. Accordingly, alarm 68 would not be activated since the patient would receive the correct dosage of fluid during flow conditions.

Figure 5A:
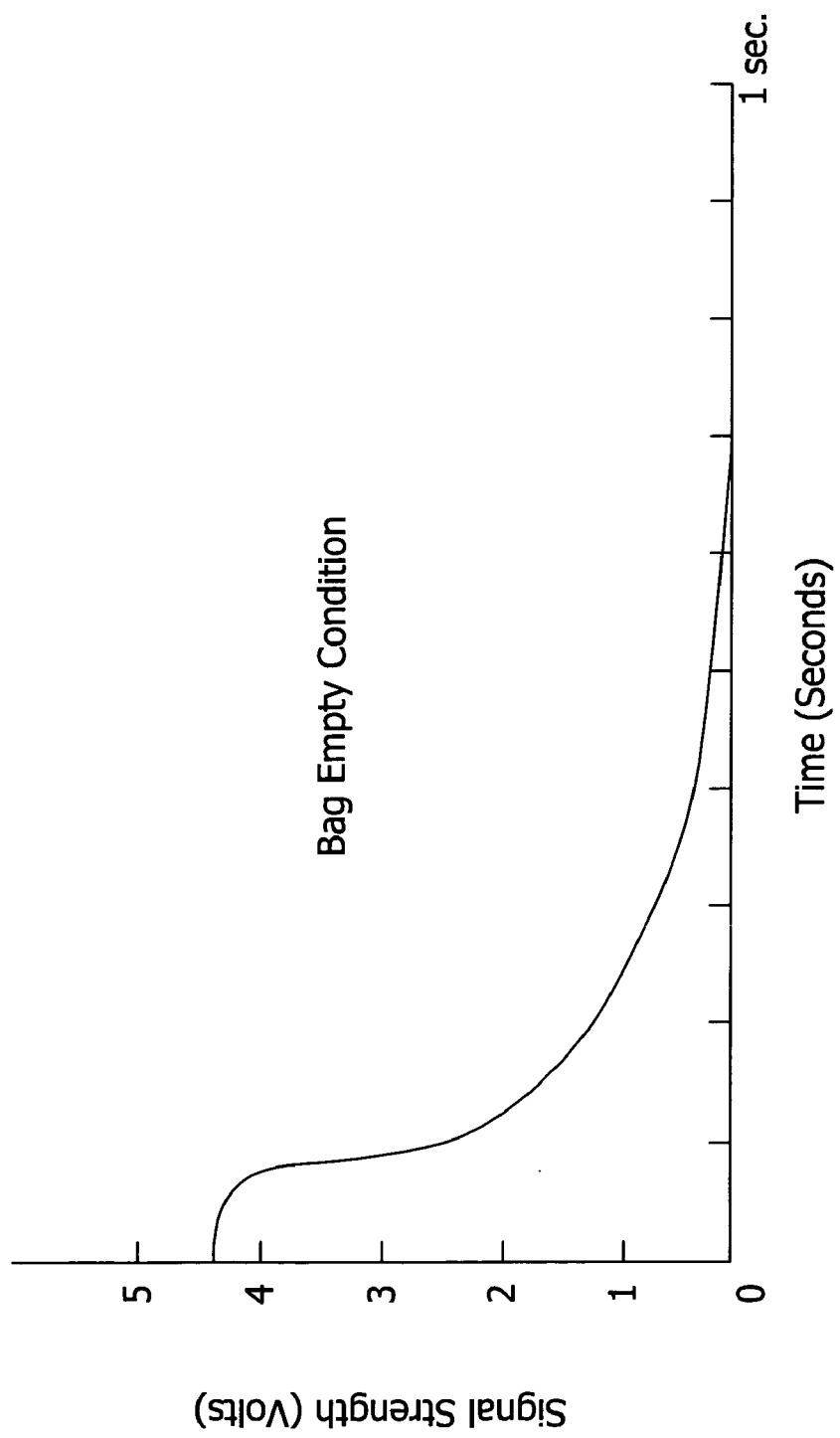
FIG. 5A is a graph illustrating the signal strength over time for a bag empty condition detected by the sensor according to the present invention.
Figure 5B:
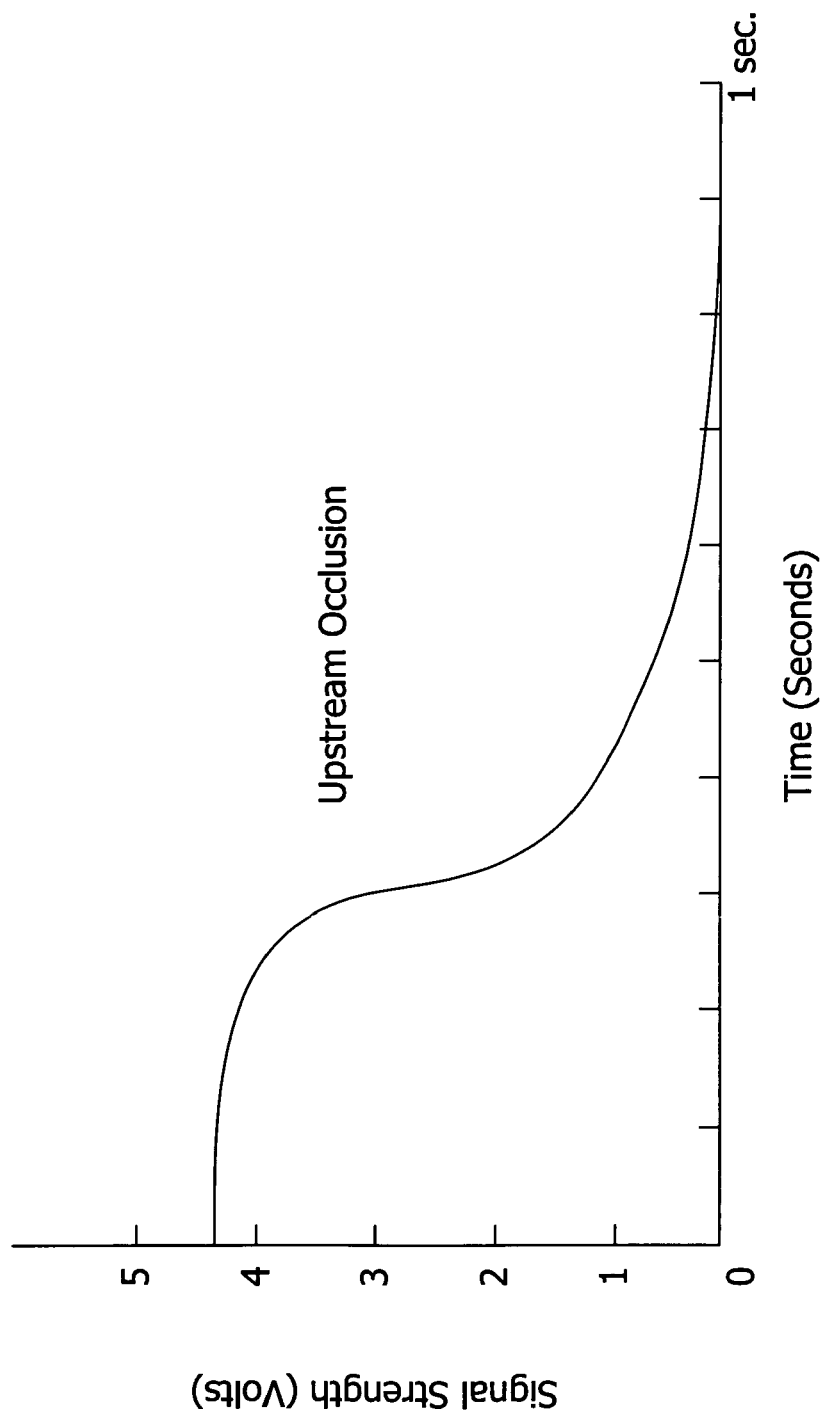
FIG. 5B is a graph illustrating the signal strength over time for an upstream occlusion detected by the sensor according to the present invention.

Flow monitoring system 12 only activates alarm 68 at decision point 314 if a bag empty condition or an occlusion along the upstream side of the administration feeding set 14 is detected as evidenced by the absence of fluid in tubing 56 during operation of the flow control apparatus 10. Software subsystem 36 distinguishes between bag empty condition and an upstream occlusion at decision point 316. As depicted in FIGS. 5A and 5B, a comparison is performed at decision point 316 in order to ascertain whether a bag empty condition or an upstream occlusion is present within administration feeding set 14.

As further shown, the graphs illustrated in FIGS. 5A and 5B provide predetermined baselines that represent the relative signal strengths of the ultrasonic signal received by the receiver assembly 30B for a bag empty condition and upstream occlusion, respectively, which provide a basis for distinguishing between these two upstream flow conditions based upon a comparison of a plurality of readings taken by single sensor 32 against the respective predetermined baseline criteria representative of these two flow abnormalities. In particular, software subsystem 36 compares the change of the signal strength from the plurality of sensor readings generated by single sensor 32 over time against the predetermined baseline criteria for these particular flow conditions. This provides a comparison with readings taken by single sensor 32 that permits the software subsystem 36 to distinguish between a bag empty and an upstream occlusion. For example, in a bag empty condition, the change between the subsequent readings would decrease more rapidly over time, while in an upstream occlusion the signal change would decrease more slowly over time. It should be noted that while the graphs in FIGS. 5A and 5B depict an example of a preferred baseline criteria, other baseline criteria which may distinguish these two flow abnormalities may be utilized.

Upon the determination that a bag empty condition is present at decision point 316 based upon signal comparison against the predetermined criteria as described above, software subsystem 36 activates alarm 68. If the software subsystem 36 determines at decision point 316 that an upstream occlusion is present, software subsystem 36 would also direct the activation of an alarm 68 indicative of such a flow abnormality.

Accordingly, the flow monitoring system 12 is capable of detecting and distinguishing between upstream and downstream flow conditions including at least four separate flow conditions that occur within an administration feeding set 14. The ability of the flow monitoring system 12 to detect and distinguish between upstream and downstream flow conditions is accomplished preferably by a single detection point by single sensor 32 positioned at the upstream side of the administration feeding set 14.

Although flow control apparatus 10 described above is an exemplary embodiment, the present invention contemplates that the flow monitoring system 12 may be used with any suitable flow control apparatus.

It should be understood from the foregoing that, while particular embodiments of the invention have been illustrated and described, various modifications can be made thereto without departing from the spirit and scope of the invention.

What is claimed is:

1. A flow control apparatus adapted to be loaded with an administration feeding set having an upstream side and a downstream side, said flow control apparatus comprising:
   a) a single ultrasonic sensor comprising a receiver assembly and an ultrasonic transmitter assembly, wherein the transmitter assembly transmits, to the receiver assembly, an ultrasonic signal through a portion of the administration feeding set,
   b) a microprocessor in operative association with the single ultrasonic sensor for receiving the ultrasonic signal from the receiver assembly, and further in operative association with a software subsystem executed on the microprocessor for detecting the presence or absence of fluid in the upstream side of said administration feeding set, and
   c) wherein the software subsystem is in operative association with the single ultrasonic sensor and configured to identify between an upstream flow occlusion and a downstream flow occlusion present within the administration feeding set, as a function of the received ultrasonic signal.

2. The flow control apparatus according to claim 1, further comprising a means for preventing fluid flow in said administration feeding set, said means for preventing fluid flow being in operative association with said software subsystem.

3. The flow control apparatus according to claim 2, wherein said software subsystem prevents fluid flow in said administration feeding set.

4. The flow control apparatus according to claim 1, wherein said software subsystem is capable of identifying whether or not a bag empty condition exists.

5. The flow control apparatus according to claim 1, wherein said software subsystem is capable of identifying whether or not normal flow exists.

6. A method of monitoring fluid flow comprising:
   a) engaging one end of an administration feeding set to at least one fluid source;
   b) loading said administration feeding set having tubing, a valve mechanism, and a mounting member, wherein said valve mechanism and mounting member are engaged to a flow control apparatus;
   c) stretching said tubing between said valve mechanism and said mounting member; and
   d) generating an ultrasonic signal by a single sensor a positioned adjacent a portion of the tubing, said ultrasonic signal being representative of a presence or absence of fluid in the portion of tubing; and
   e) executing a software subsystem on a microprocessor to identify between an upstream occlusion and a downstream occlusion present within said administration feeding set, wherein the microprocessor is operatively connected to the single sensor for receiving the ultrasonic signal and detecting the presence or absence of fluid in the upstream side of the feeding set as a function of the ultrasonic signal, and further wherein the software subsystem uses the ultrasonic signal to determine the upstream and downstream occlusion.

7. The method according to claim 6, further comprising preventing fluid flow in said administration feeding set to identify said downstream occlusion present in said administration feeding set.

8. The method according to claim 6, wherein another end of said administration feeding set is engaged to a patient.

9. The method according to claim 6, wherein executing the software subsystem further comprises identifying whether or not a bag empty condition exists.

10. The method according to claim 6, wherein executing the software subsystem further comprises identifying whether or not normal flow exists.

* * * * *